(12) United States Patent
Kent

(10) Patent No.: US 9,808,620 B2
(45) Date of Patent: Nov. 7, 2017

(54) METHOD AND APPARATUS FOR TREATING RESTLESS LEGS SYNDROME

(71) Applicant: Invicta Medical, Inc., Portola Valley, CA (US)

(72) Inventor: Steven Thomas Kent, Portola Valley, CA (US)

(73) Assignee: INVICTA MEDICAL, INC., Portola Valley, CA (US)

( * ) Notice: Subject to any disclaimer, the term of this patent is extended or adjusted under 35 U.S.C. 154(b) by 0 days.

(21) Appl. No.: 15/491,910

(22) Filed: Apr. 19, 2017

(65) Prior Publication Data

US 2017/0216586 A1 Aug. 3, 2017

Related U.S. Application Data

(62) Division of application No. 15/173,649, filed on Jun. 4, 2016.

(60) Provisional application No. 62/171,218, filed on Jun. 4, 2015.

(51) Int. Cl.
*A61N 1/00* (2006.01)
*A61N 1/36* (2006.01)
*A61N 1/04* (2006.01)

(52) U.S. Cl.
CPC ....... *A61N 1/36003* (2013.01); *A61N 1/0456* (2013.01); *A61N 1/0484* (2013.01); *A61N 1/36014* (2013.01)

(58) Field of Classification Search
CPC ............ A61N 1/36003; A61N 1/36014; A61N 1/0484; A61N 1/0456
See application file for complete search history.

(56) References Cited

U.S. PATENT DOCUMENTS

| 4,558,704 | A | * | 12/1985 | Petrofsky | A61F 2/68 607/48 |
| 7,369,896 | B2 | * | 5/2008 | Gesotti | A61N 1/36003 607/45 |
| 8,620,438 | B1 | | 12/2013 | Wijting et al. | |
| 8,768,474 | B1 | | 7/2014 | Thompson et al. | |
| 2004/0147975 | A1 | | 7/2004 | Popovic et al. | |
| 2008/0208287 | A1 | | 8/2008 | Palermo et al. | |
| 2009/0221943 | A1 | | 9/2009 | Burbank et al. | |
| 2010/0023103 | A1 | | 1/2010 | Elborno | |
| 2010/0152808 | A1 | | 6/2010 | Boggs, II | |

(Continued)

OTHER PUBLICATIONS

International Search Report and Written Opinion dated Sep. 8, 2016, serial No. PCT/US16/35936, filed Jun. 4, 2016, 11 pages.

*Primary Examiner* — Mallika D Fairchild
(74) *Attorney, Agent, or Firm* — Paradice and Li LLP

(57) ABSTRACT

Apparatuses and methods are disclosed that may be used to treat one or more restless leg syndrome (RLS) symptoms of a patient. One example method may include generating first and second stimulation waveforms using a waveform generator; electrically stimulating at least a portion of a sacral region of the patient, based on the first and second stimulation waveforms, using a number of electrodes; damping or interfering with electrical signals transmitted from the patient's brain to the patient's legs via a femoral nerve of the patient using the electrical stimulation; and reducing the one or more symptoms of RLS based on damping or interfering with the electrical signals transmitted from the patient's brain.

26 Claims, 13 Drawing Sheets

(56) References Cited

U.S. PATENT DOCUMENTS

2010/0280570 A1 11/2010 Sturm et al.
2015/0134028 A1 5/2015 Kaula et al.
2016/0235981 A1 8/2016 Southwell et al.

* cited by examiner

METHOD AND APPARATUS FOR TREATING RESTLESS LEGS SYNDROME

CROSS-REFERENCE TO RELATED APPLICATIONS

This application claims priority to co-pending and commonly owned U.S. patent application Ser. No. 15/173,649 entitled "METHOD AND APPARATUS FOR TREATING RESTLESS LEGS SYNDROME" filed on Jun. 4, 2016, which claims priority to U.S. Provisional Patent Application No. 62/171,218 entitled "METHOD AND APPARATUS FOR TREATING RESTLESS LEGS SYNDROME" filed on Jun. 4, 2015, the entireties of both of which are incorporated by reference herein.

TECHNICAL FIELD

The present embodiments relate generally to restless legs syndrome (RLS), and specifically to non-invasive techniques for treating one or more symptoms of RLS.

BACKGROUND OF RELATED ART

Restless legs syndrome (RLS), also known as Willis-Ekbom disease (WED), is a neurological disorder characterized by an irresistible urge to move one's body to stop uncomfortable or odd sensations. It most commonly affects the legs, but can affect the arms, torso, and even phantom limbs. RLS sensations range from pain or an aching in the muscles, to "an itch you can't scratch," an unpleasant "tickle that won't stop," or even a "crawling" feeling. The sensations typically begin or intensify during quiet wakefulness, such as when relaxing, reading, studying, or trying to sleep. For example, sitting or lying down (e.g., reading, plane ride, watching TV) can trigger the sensations and urge to move. These symptoms of RLS can make sleeping difficult for many patients and a recent poll shows the presence of significant daytime difficulties resulting from this condition. Additionally, most individuals with RLS suffer from periodic limb movement disorder (PLMD), which is an objective physiologic marker of the disorder and is associated with sleep disruption.

Movement usually brings immediate relief, although temporary and partial. Continuous, fast up-and-down movements of the leg, and/or rapidly moving the legs toward then away from each other, may keep sensations at bay without having to walk. The sensations—and the need to move—may return immediately after ceasing movement or at a later time. RLS may start at any age, including childhood, and is a progressive disease for most individuals.

Primary RLS is considered idiopathic or with no known cause. Primary RLS usually begins slowly, before approximately 40-45 years of age and may disappear for months or even years. It is often progressive and gets worse with age. RLS in children is often misdiagnosed as growing pains. Secondary RLS often has a sudden onset after age 40, and may occur daily from the beginning. It is most associated with specific medical conditions or the use of certain drugs.

Treatment is often with levodopa or a dopamine agonist. These hypotheses are based on the observation that iron and levodopa, a pro-drug of dopamine that can cross the blood-brain barrier and is metabolized in the brain into dopamine (as well as other mono-amine neurotransmitters of the catecholamine class) can be used to treat RLS, levodopa being a medicine for treating hypo-dopaminergic (low dopamine) conditions such as Parkinson's disease.

RLS drug therapy is not curative and has side effects such as nausea, dizziness, hallucinations, orthostatic hypotension, or daytime sleep attacks. There are, however, issues with the use of dopamine agonists including augmentation. This is a medical condition in which the drug itself causes symptoms to increase in severity and/or occur earlier in the day. Dopamine agonists may also cause rebound, when symptoms increase as the drug wears off. In many cases, the longer dopamine agonists are used the higher the risk of augmentation and rebound as well as the severity of the symptoms. A recent study has indicated that dopamine agonists used in restless leg syndrome may lead to an increase in compulsive gambling.

Thus, there is a need for more effective treatment of the RLS without the undesirable side effects of drugs currently used for RLS treatment.

SUMMARY

This Summary is provided to introduce in a simplified form a selection of concepts that are further described below in the Detailed Description. This Summary is not intended to identify key features or essential features of the claimed subject matter, nor is it intended to limit the scope of the claimed subject matter.

Apparatuses and methods are disclosed that may be used to treat one or more restless leg syndrome (RLS) symptoms of a patient. For some embodiments, the method may include generating first and second stimulation waveforms using a waveform generator; electrically stimulating at least a portion of a sacral region of the patient, based on the first and second stimulation waveforms, using a number of electrodes; and damping or interfering with electrical signals transmitted from the patient's brain to the patient's legs via a femoral nerve of the patient using the electrical stimulation. In some aspects, the electrically stimulating may be performed by inducing the first electrical current to flow between the first electrode and the third electrode based on the first stimulation waveform, and by inducing the second electrical current to flow between the second electrode and the fourth electrode based on the second stimulation waveform. The method may also include reducing one or more symptoms of RLS based on damping or interfering with the electrical signals transmitted from the patient's brain.

In another example, a system for treating one or more RLS symptoms of a patient is disclosed. The system may include a waveform generator and a number of electrodes. For some embodiments, the system may include four electrodes (e.g., first, second, third, and fourth electrodes), and the waveform generator may be configured to generate first and second stimulation waveforms. The first electrode may be positioned on a left portion of the patient's lumbar region and configured to receive the first stimulation waveform on a first channel. The second electrode may be positioned on a right portion of the patient's lumbar region and configured to receive the second stimulation waveform on a second channel. The third electrode may be positioned over an upper rear portion of the patient's right leg and configured to receive the first stimulation waveform on the first channel. The fourth electrode may be positioned over an upper rear portion of the patient's left leg and configured to receive the second stimulation waveform on the second channel. The first, second, third, and fourth electrodes may be configured to electrically stimulate at least a portion of a femoral nerve of the patient based on the first and second stimulation waveforms. The electrical stimulation may be configured to dampen or interfere with electrical signals transmitted from the patient's brain to the patient's legs via the femoral nerve in a manner that reduces and/or prevents on the onset of one or more RLS symptoms.

BRIEF DESCRIPTION OF THE DRAWINGS

The present embodiments are illustrated by way of example and are not intended to be limited by the figures of the accompanying drawings, where like reference numerals refer to corresponding parts throughout the drawing figures.

DETAILED DESCRIPTION

Figure 1A:
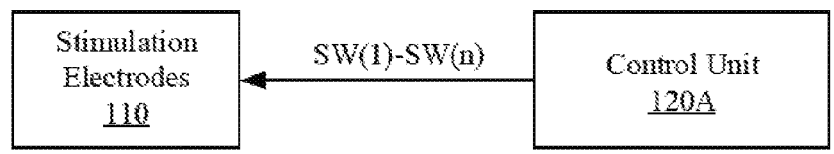
FIG. 1A is a block diagram of one RLS treatment system in accordance with example embodiments.

Non-invasive apparatuses and method for treating restless legs syndrome (RLS) are disclosed herein. In the following description, numerous specific details are set forth to provide a thorough understanding of the present disclosure. Also, in the following description and for purposes of explanation, specific nomenclature is set forth to provide a thorough understanding of the present embodiments. However, it will be apparent to one skilled in the art that these specific details may not be required to practice the present embodiments. In other instances, well-known circuits and devices are shown in block diagram form to avoid obscuring the present disclosure. The term "coupled" as used herein means connected directly to or connected through one or more intervening components, circuits, or physiological matter. Any of the signals provided over various buses described herein may be time-multiplexed with other signals and provided over one or more common buses. Additionally, the interconnection between circuit elements or software blocks may be shown as buses or as single signal lines. Each of the buses may alternatively be a single signal line, and each of the single signal lines may alternatively be buses, and a single line or bus might represent any one or more of a myriad of physical or logical mechanisms for communication between components. Further, the logic levels and timing assigned to various signals in the description below are arbitrary and/or approximate, and therefore may be modified (e.g., polarity reversed, timing modified, etc.) as desired.

As used herein, the term "substantially lateral direction" refers to a direction across a patient's body in a side-to-side manner, and the term "substantially vertical direction" refers to a direction across a patient's body in a top-to-bottom. Further, the term "substantially diagonal direction" refers to a direction across a patient's body in both a side-to-side manner and a top-to-bottom manner (e.g., a diagonal direction may be approximately 45 degrees with respect to the substantially lateral direction and the substantially vertical direction. Further, as used herein, the term "reversible current" means a current that may change or reverse polarity from time to time between two controllable voltage potentials.

Further, some example embodiments may utilize wireless communication signals including, for example, WLAN and Bluetooth signals. As used herein, the terms "WLAN" and "Wi-Fi®" may include communications governed by the IEEE 802.11 family of standards, HiperLAN (a set of wireless standards, comparable to the IEEE 802.11 standards, used primarily in Europe), and other technologies having relatively short radio propagation range. Further, as used herein, the term BLUETOOTH® (Bluetooth) may include communications governed by the Bluetooth Special Interest Group.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present application, discussions utilizing the terms such as "accessing," "receiving," "sending," "using," "selecting," "determining," "normalizing," "multiplying," "averaging," "monitoring," "comparing," "applying," "updating," "measuring," "deriving," or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage transmission or display devices.

In the figures, a single block may be described as performing a function or functions; however, in actual practice, the function or functions performed by that block may be performed in a single component or across multiple components, and/or may be performed using hardware, using software, or using a combination of hardware and software. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. Also, the example wireless communications devices may include components other than those shown, including well-known components such as a processor, memory and the like.

The techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory computer-readable storage medium comprising instructions that, when executed, performs one or more of the methods described above. The non-transitory computer-readable data storage medium may form part of a computer program product, which may include packaging materials.

The non-transitory computer-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor.

The various illustrative logical blocks, modules, circuits and instructions described in connection with the embodiments disclosed herein may be executed by one or more processors, such as one or more digital signal processors (DSPs), general purpose microprocessors, application specific integrated circuits (ASICs), application specific instruction set processors (ASIPs), field programmable gate arrays (FPGAs), or other equivalent integrated or discrete logic circuitry. The term "processor," as used herein may refer to any of the foregoing structure or any other structure suitable for implementation of the techniques described herein. In addition, in some aspects, the functionality described herein may be provided within dedicated software modules or hardware modules configured as described herein. Also, the techniques could be fully implemented in one or more circuits or logic elements. A general purpose processor may be a microprocessor, but in the alternative, the processor may be any conventional processor, controller, microcontroller, or state machine. A processor may also be implemented as a combination of computing devices (e.g., a combination of a DSP and a microprocessor, a plurality of microprocessors, one or more microprocessors in conjunction with a DSP core, or any other such configuration).

At present, there is no known cause or cure for RLS. As mentioned above, RLS drug therapy is not curative and has side effects such as nausea, dizziness, hallucinations, orthostatic hypotension, and/or daytime sleep attacks. In addition, current RLS drug therapy (e.g., dopamine agonists) often causes augmentation and rebound, which in turn may create an endless degenerative cycle in which RLS patients need larger and larger doses of drugs to relieve the symptoms of RLS (which in turn tends to worsen the frequency and severity of the symptoms of RLS). These are at least some of the technical problems to be solved by the example embodiments.

Applicant has discovered that the symptoms of RLS may be alleviated, without the use of drugs such as dopamine agonists, by electrical stimulation of one or more regions of a patient's body. More specifically, in accordance with example embodiments, the severity and frequency of involuntary leg twitching and/or leg jerking associated with RLS may be reduced and, in some instances, completely eliminated by transcutaneously applying a number of electrical currents in selected patterns across a portion of a patient's midsection. For at least one example embodiment, electrical currents transcutaneously applied in complementary and substantially diagonal directions (e.g., in a criss-cross pattern) across the sacral region of a patient may dampen undesirable electrical signals transmitted from the patient's brain to the patient's legs, thereby reducing the severity and frequency of such involuntary leg twitching and/or leg jerking. In some instances, the electrical currents transcutaneously applied by the example embodiments may prevent such undesirable electrical signals originating in the patient's brain from reaching the patient's legs, thereby eliminating such involuntary leg twitching and/or leg jerking altogether.

These and other details of the example embodiments, which provide one or more technical solutions to the aforementioned technical problems, are described in more detail below.

FIG. 1A shows a block diagram of an RLS treatment system 100 in accordance with the example embodiments. System 100 is shown to include a control unit 120A and a number of stimulation electrodes 110. Control unit 120A may include any suitable waveform generator configured to generate a number of stimulation waveforms SW(1)-SW(n). The number of stimulation waveforms SW(1)-SW(n) may be transmitted to the stimulation electrodes 110 on one or more channels. In response to the stimulation waveforms SW(1)-SW(n), the stimulation electrodes 110 may transcutaneously apply one or more electrical currents in one or more selected patterns across selected portions of the patient's skin. The transcutaneously applied electrical currents may be configured to electrically stimulate a femoral nerve of the patient, for example, to dampen and/or interfere with electrical signals transmitted from the patient's brain to the patient's legs via the femoral nerve. As described in more detail below, dampening and/or interfering with electrical signals transmitted from the patient's brain to the patient's legs via the femoral nerve may not only reduce the severity of one or more RLS symptoms but may also prevent the onset of one or more RLS symptoms.

In some aspects, the control unit 120A may be a Transcutaneous Electrical Nerve Stimulation (TENS) unit that can modulate the pulse width, the frequency, and the intensity of the transcutaneously applied electrical currents. More specifically, for one example embodiment, the control unit 120A is a 2-channel TENS unit (e.g., commercially available from Mettler Electronics Corp) that may be programmed to generate first and second independent stimulation waveforms SW1 and SW2 on first and second channels. The first stimulation waveform SW1 may be provided to a first pair of electrodes 110 via a first channel, and the second stimulation waveform SW2 may be provided to a second pair of electrodes 110 via a second channel, as described in more detail below. For one implementation, the independent stimulation waveforms SW1 and SW2 may each have a frequency of approximately 200 Hz, a pulse width of approximately 250 microseconds, and a current between approximately 8 and 12 milliamps. For other embodiments, other frequencies, pulse widths, and currents may be used.

Figure 1B:
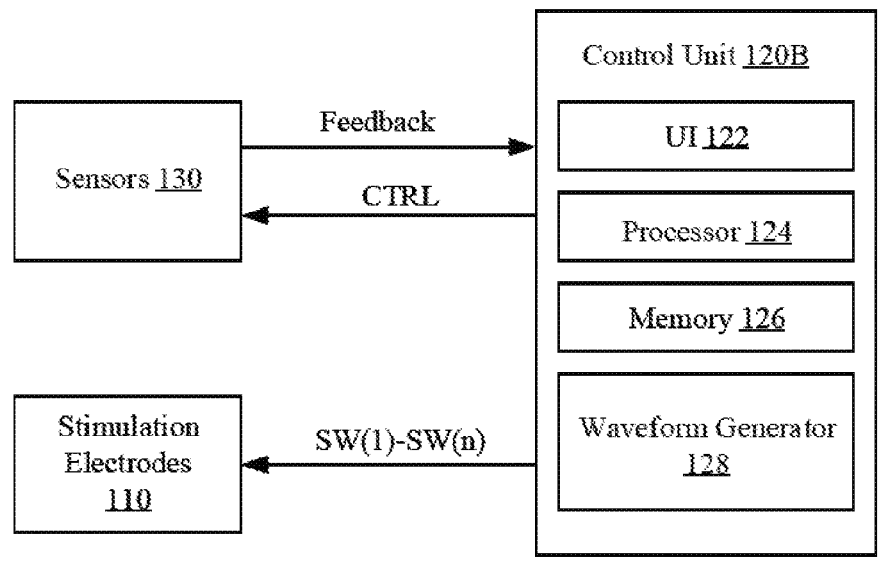
FIG. 1B is a block diagram of another RLS treatment system in accordance with example embodiments.

FIG. 1B shows a block diagram of another RLS treatment system 101 in accordance with the example embodiments. System 101 is shown to include the stimulation electrodes 110, a control unit 120B, and a number of sensors 130. The sensors 130 are adapted to be positioned at various locations of the patient's body, for example, to detect the onset, severity, frequency, duration, and/or cessation of involuntary leg twitching, leg jerking, and/or other periodic limb movements associated with RLS. The sensors 130, which may be coupled to control unit 120B via any suitable connection (e.g., conductive wires or cables) may provide feedback information to the control unit 120B. In response thereto, the control unit 120B may commence, adjust, and/or terminate the transcutaneous application of electrical currents by electrodes 110, for example, by controlling the stimulation waveforms SW(1)-SW(n) provided to the electrodes 110. In addition, the one or more sensors 130 may receive control signals CTRL from the control unit 120B.

The sensors 130 may be any suitable sensing devices that can detect movement of one or more of an RLS patient's limbs. For at least one example embodiment, the sensors 130 are accelerometers. For some embodiments, the sensors 130 may also include microphones.

The control unit 120B is shown in FIG. 1B as including a user interface (UI) 122, a processor 124, a memory 126, and a waveform generator 128. The UI 122 may be used by an RLS patient (or another person) to control overall operation of the control unit 120B and/or to receive feedback information (e.g., diagnostic information, historical data, efficacy data, trending information) regarding the use and effectiveness of the RLS treatment system 101. The processor 124 may be any one or more suitable processors capable of executing scripts or instructions of one or more software programs stored in the control unit 120B (e.g., within memory 126).

The memory 126, which may be any suitable memory or storage device, may store one or more software programs that, when executed by processor 124, may control the transcutaneous application of electrical currents to treat RLS as described herein. The memory 126 may also store data corresponding to the RLS patient's limb movements relative to the transcutaneous application of electrical currents by the stimulation electrodes 110, for example, to determine effectiveness of the treatment and/or to determine optimal settings (e.g., frequency, pulse width, and current) of the stimulation waveforms as well as optimal positioning of the electrodes 110 on the patient.

The waveform generator 128 may be used to generate the stimulation waveforms SW(1)-SW(n) provided to the electrodes 110. The waveform generator 128 may be any suitable signal generator, and is thus not described in detail herein. In some aspects, the waveform generator 128 may be the waveform generator provided within the control unit 120A of FIG. 1A. The stimulation waveforms generated by the waveform generator 128 may include continuous (analog) voltage or current waveforms, may include any number of pulses that may vary in shape and duration as a pulse train, or the pulses may be combined to simulate an analog waveform or a combination of both, and may be dynamically modified by the waveform generator 128. In addition, for some embodiments, the waveform generator 128 may be configured to periodically reverse the polarity or direction of the transcutaneously applied electrical currents, for example, so that that the stimulation waveforms are zero sum drive waveforms (e.g., to minimize or preclude electrochemical activity and/or to minimize the patient's awareness of any electrical activity related to the RLS treatment systems disclosed herein).

The processor 124 may instruct the waveform generator 128 to adjust the settings (e.g., frequency, pulse width, and current) of the stimulation waveforms based on the feedback from the sensors. For example, if the electrical stimulation provided by system 101 is not reducing the involuntary limb movements below a threshold, the processor 124 may instruct the waveform generator 128 to increase the current, frequency, and/or pulse width of the stimulation waveforms (which in turn may increase electrical stimulation of the nerves surrounding and/or exiting from the patient's spinal column). In addition, the processor 124 may instruct the waveform generator 128 to selectively terminate the generation of the stimulation waveforms based on the feedback from sensors 130, for example, to conserve power and/or to minimize or cease electrical stimulation for durations of time when no RLS symptoms are present and/or when the patient is asleep.

Figure 1C:
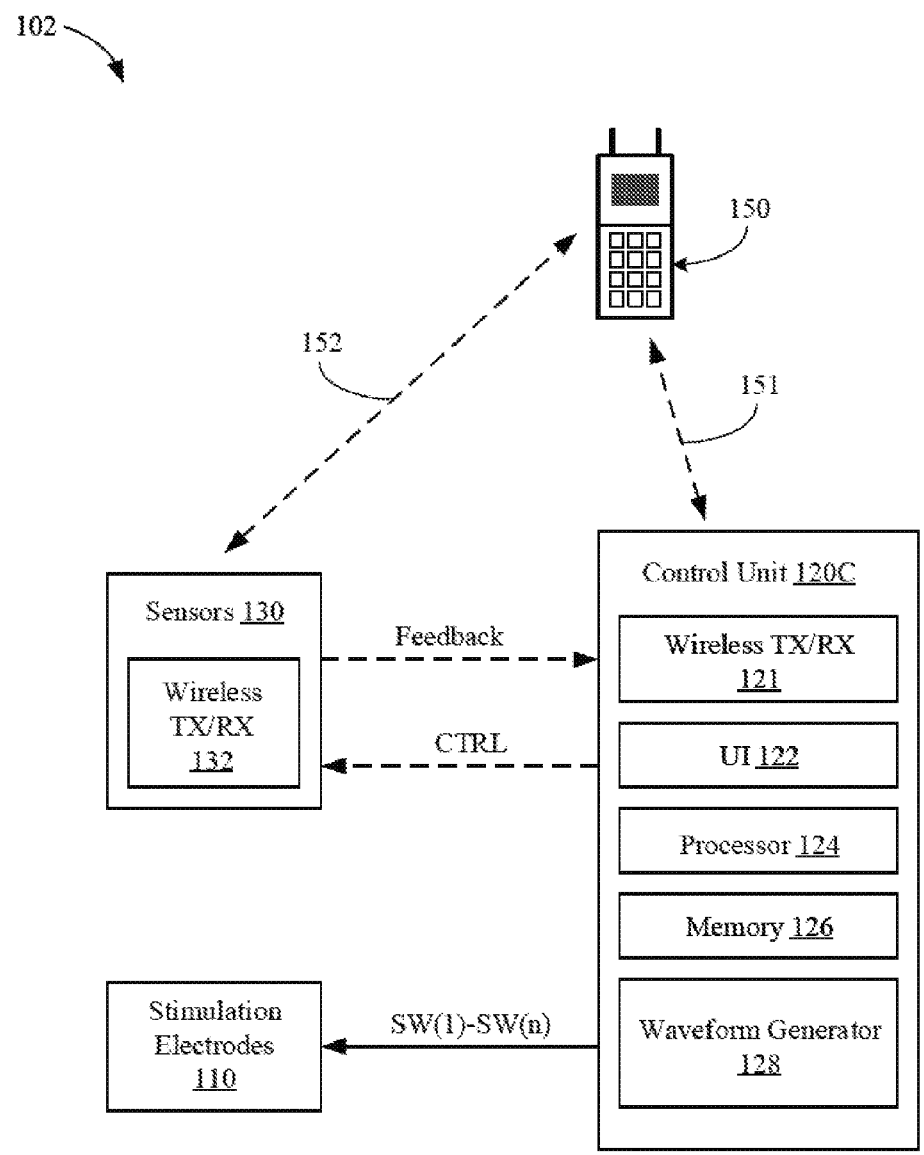
FIG. 1C is a block diagram of yet another RLS treatment system in accordance with example embodiments.

FIG. 1C shows a block diagram of another RLS treatment system 102 in accordance with the example embodiments. System 102 is shown to include the stimulation electrodes 110, a control unit 120C, the number of sensors 130, and a mobile communication device 150. The mobile computing device 150 may be any suitable wireless device including, for example, a smartphone, personal digital assistants (PDAs), tablet devices, laptop computers, smart watches, or the like. Although not shown for simplicity, the mobile computing device 150 may include a transceiver, one or more processing resources (e.g., processors and/or ASICs), one or more memory resources, and a power source (e.g., a battery). The memory resources may include a non-transitory computer-readable medium (e.g., one or more nonvolatile memory elements, such as EPROM, EEPROM, Flash memory, a hard drive, etc.) that stores instructions for performing operations described herein. The memory resources of mobile computing device 150 may also store, for execution by the one or more processing resources, an application (e.g., a "mobile app") that can wirelessly control operation of control unit 120C via a wireless connection 151 and/or receive feedback information from control unit 120C and/or sensors 130 via a wireless connection 152.

The sensors 130 of FIG. 1C may include a wireless transceiver 132 to wirelessly transmit the feedback information to control unit 120C and/or to wirelessly receive control signals CTRL from control unit 120C. The wireless transceiver 132 may also be used to wirelessly communicate with mobile computing device 150.

The control unit 120C includes all the components of control unit 120B of FIG. 1B, plus a wireless transceiver 121 to wirelessly transmit control signals CTRL to sensors 130, to wirelessly receive feedback information from sensors 130, and to wireless communicate with the mobile computing device 150.

The wireless transceiver 121 and 132 (as well as the wireless transceiver included within mobile computing device 150), may include one or more Wi-Fi transceivers, Bluetooth transceivers, cellular transceivers, and/or other suitable radio frequency (RF) transceivers to transmit and receive wireless communication signals. Each transceiver may wirelessly communicate with other devices in distinct operating frequency bands and/or using distinct communication protocols.

Figure 2A:
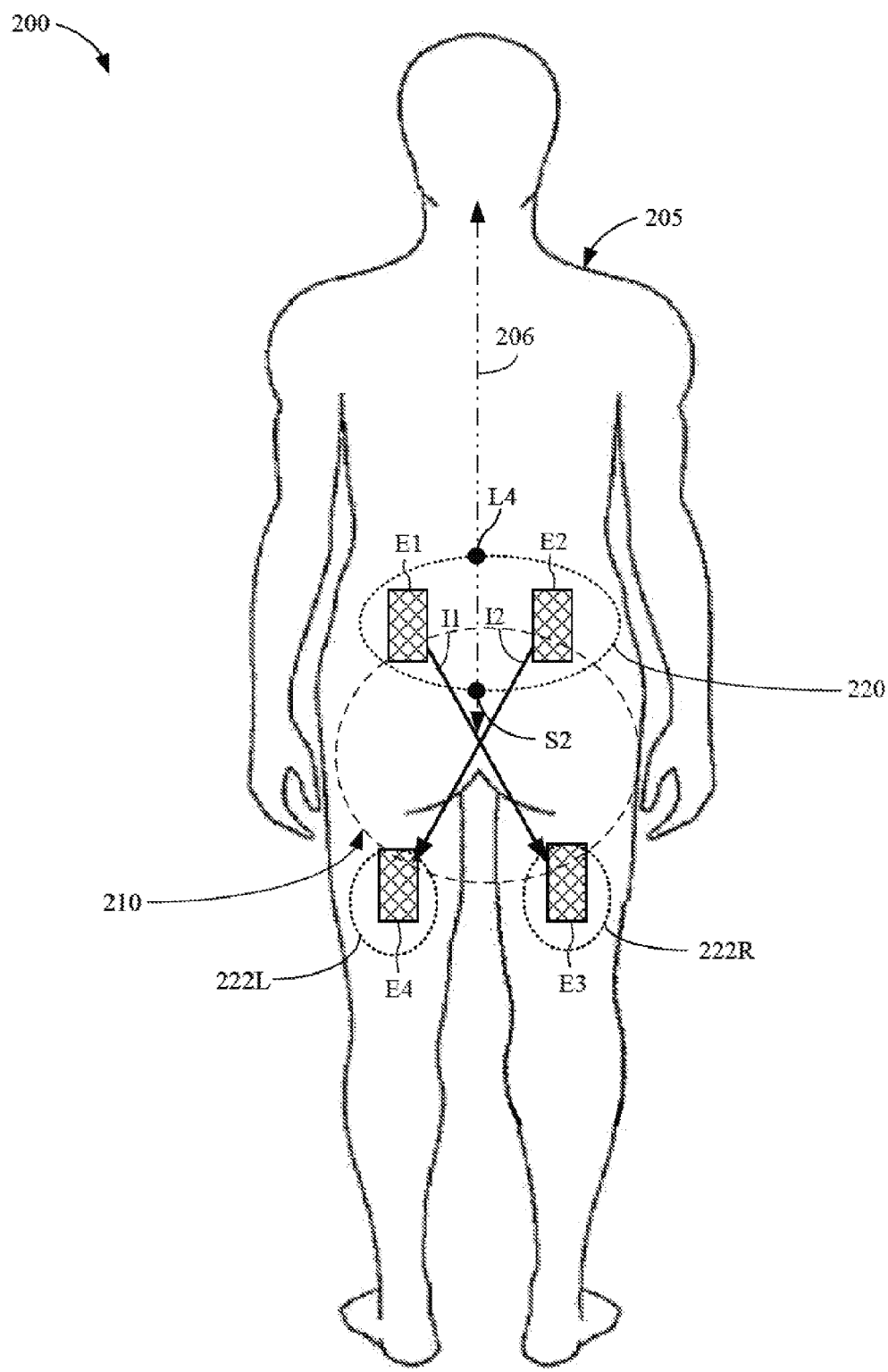
FIG. 2A depicts one example placement of electrodes on a patient in accordance with example embodiments.

FIG. 2A is a depiction 200 of an example placement of four electrodes E1-E4 on the back side of a patient 205. Although not shown in FIG. 2A for simplicity, the four electrodes E1-E4 may be electrically coupled to waveform generator 128 of FIGS. 1A-1C using any suitable wired or wireless connection. As described above, the first electrode E1 and the third electrode E3 may be configured to receive a first stimulation waveform from waveform generator 128 on a first channel, and the second electrode E2 and the fourth electrode E4 may be configured to receive a second stimulation waveform from waveform generator 128 on a second channel.

The four electrodes E1-E4, which are one embodiment of stimulation electrodes 110 of FIG. 1A, may be adapted to be positioned in an "X" formation or pattern that may be substantially centered at the patient's sacrum. The four electrodes E1-E4 may be configured to electrically stimulate one or more of the patient's nerves within the patient's sacral region 210 based on the first and second stimulation waveforms. More specifically, for at least implementations, the four electrodes E1-E4 may electrically stimulate the femoral nerve at or near its exit from the patient's spinal column based on the first and second stimulation waveforms. As explained in more detail below, electrically stimulating the femoral nerve at or near its exit from the spinal column may dampen, block, and/or interfere with electrical signals transmitted from the patient's brain to the legs via the femoral nerve in a manner that not only reduces the severity of RLS symptoms but that may also prevent the onset of RLS symptoms.

Although not shown in FIG. 2A for simplicity, the four electrodes E1-E4 may be electrically coupled to the control unit 120 (e.g., where "control unit 120" may refer to one or more of control units 120A-120C described above with respect to FIGS. 1A-1C, respectively), for example, using electrical conductors, wires, cables, or the like. For example, electrodes E1 and E3 may be a first pair of electrodes that are coupled to a first channel of a 2-channel TENS unit via a first pair of conductive wires, and electrodes E2 and E4 may be a second pair of electrodes that are coupled to a second channel of the 2-channel TENS unit via a second pair of conductive wires. For one example embodiment, electrodes E1-E4 may be self-adhering TENS electrodes measuring approximately 2 inches wide and 3.5 inches long (although for other embodiments, other sizes and/or types of electrodes may be used for electrodes E1-E4). Although not shown for simplicity, each of the electrodes E1-E4 may be electrically coupled to a suitable waveform generator (e.g., the waveform generator 128 of FIGS. 1B and 1C) via electrically conductive wires, cables, and/or any other suitable conductive material.

For some implementations, the first and second electrodes E1 and E2 may be positioned on either side of the patient's spine 206 in the lumbar region, the third electrode E3 may be positioned on an upper rear portion of the patient's right leg, and the fourth electrode E4 may be positioned on an upper rear portion of the patient's left leg. As used herein, the term "upper rear portion" may refer to the portion of the patient's leg between the knee and buttocks. In some aspects, the first and second electrodes E1 and E2 may be positioned on opposite sides (e.g., left and right sides, respectively) of the patient's lumbar region 220, and the third and fourth electrodes E3 and E4 may be positioned over at least a portion of the patient's right hamstring 222R and left hamstring 222L, respectively. More specifically, the first and second electrodes E1 and E2 may be positioned in regions of the patient's back between the L4 vertebrae and the S2 vertebrae, the third electrode E3 may be positioned on a rear portion of the right leg approximately equidistant between the right knee and buttocks, and the fourth electrode E4 may be positioned on a rear portion of the left leg approximately equidistant between the left knee and buttocks.

For other embodiments, the first and second electrodes E1 and E2 may be positioned in regions of the patient's back higher than L4 or lower than S2, and the third and fourth electrodes E3 and E4 may be positioned either closer to the buttocks or closer to the knees, for example, as may depend upon the electrical, nerve, bone, and/or other characteristics of a given patient.

In operation, the first and third electrodes E1 and E3 may be connected to the control unit 120 in a manner that allows a first stimulation waveform generated by the waveform generator 128 to transcutaneously apply a first electrical current I1 between the first and third electrodes E1 and E3, and the second and fourth electrodes E2 and E4 may be connected to the control unit 120 in a manner that allows a second stimulation waveform generated by the waveform generator 128 to transcutaneously apply a second electrical current I2 between the second and fourth electrodes E2 and E4. As depicted in FIG. 2A, the first electrical current I1 is transcutaneously applied in a first substantially diagonal direction between the first and third electrodes E1 and E3, and the second electrical current I2 is transcutaneously applied in a second substantially diagonal direction between the second and fourth electrodes E2 and E4. In some aspects, the first substantially diagonal direction is approximately orthogonal to the second substantially diagonal direction. In other aspects, the direction of currents it and I2 may be the opposite or reverse of direction of currents I1 and I2 depicted in FIG. 2A.

At least one unexpected result of the transcutaneous application of the electrical currents I1 and I2 depicted in FIG. 2A is the significant reduction in severity and frequency of involuntary leg twitching and/or leg jerking associated with RLS. More specifically, Applicant believes that the transcutaneous application of electrical currents I1 and I2 in the sacral region of an RLS patient in a selected pattern (e.g., depicted in FIG. 2A) electrically stimulates the nerves surrounding and/or exiting from the patient's spinal column (e.g., between approximately L2 and S5) in a manner that dampens and/or interferes with undesirable electrical impulses in the nerves that are responsible for causing involuntary leg twitching and/or leg jerking associated with RLS. Thus, by damping and/or interfering with undesirable electrical impulses transmitted from the patient's brain to the patient's legs, the example embodiments may reduce the severity of one or more RLS symptoms and/or may prevent the onset of one or more RLS symptoms.

For other embodiments, the control unit 120 may selectively alternate directions of the transcutaneously applied electrical currents I1 and I2, for example, in a rotating manner between the electrodes E1-E4. For example, during a first time interval, control unit 120 may direct the first current I1 from electrode E1 to electrode E3, and direct the second current I2 from electrode E2 to electrode E4, as described above with respect to FIG. 2A. Then, during a second time interval, control unit 120 may direct the first current I1 from electrode E1 to electrode E4, and direct the second current I2 from electrode E2 to electrode E3. Alternatively or as an addition, control unit 120 may, during a third time interval, direct the first current I1 from electrode E1 to electrode E2, and direct the second current I2 from electrode E2 to electrode E4. This cycle may be repeated.

Figure 2B:
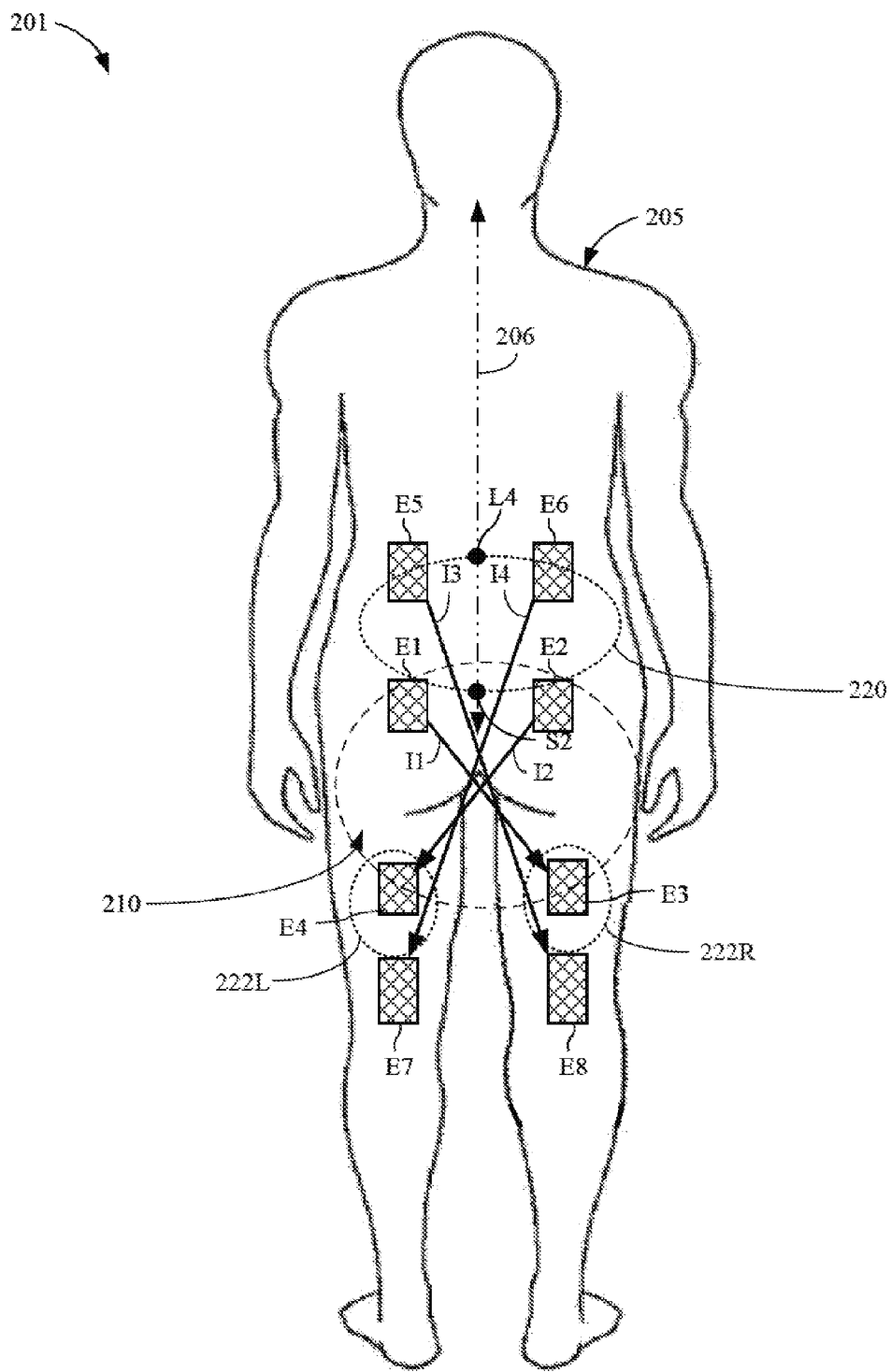
FIG. 2B depicts another example placement of electrodes on a patient in accordance with example embodiments.

Although FIG. 2A depicts four electrodes E1-E4 positioned on the patient's back in a specific pattern, the number of electrodes and their positions may vary for other embodiments. For example, FIG. 2B is a depiction 201 of an example placement of eight electrodes E1-E8 on the patient's back. The first set of four electrodes E1-E4 are positioned in an "X" formation that may be substantially centered at the patient's sacrum and generally produce electrical stimulation of the patient's nerves in a sacral region 210 of the patient, as described above with respect to FIG. 2A. The second set of four electrodes E5-E8 are also positioned in an "X" formation that may be substantially centered at the patient's sacrum and generally produce electrical stimulation of the patient's nerves in the sacral region 210 of the patient; however, the second set of four electrodes E5-E8, which facilitate the transcutaneous application of third and fourth electrical currents I3 and I4 in the manner depicted in FIG. 2B, are positioned in a much larger pattern. Specifically, the fifth electrode E5 may be positioned several inches above the first electrode E1, the sixth electrode E6 may be positioned several inches above the second electrode E2, the seventh electrode E7 may be positioned several inches below the fourth electrode E4, and the eighth electrode E8 may be positioned several inches below the third electrode E3. In this manner, one or more nerves (e.g., the femoral nerve) existing from the patient's spinal column may be electrically stimulated based on two overlapping sets of transcutaneously applied electrical currents (i.e., the first set including currents I1-I2, and the second set including currents I3-I4).

Figure 3A:
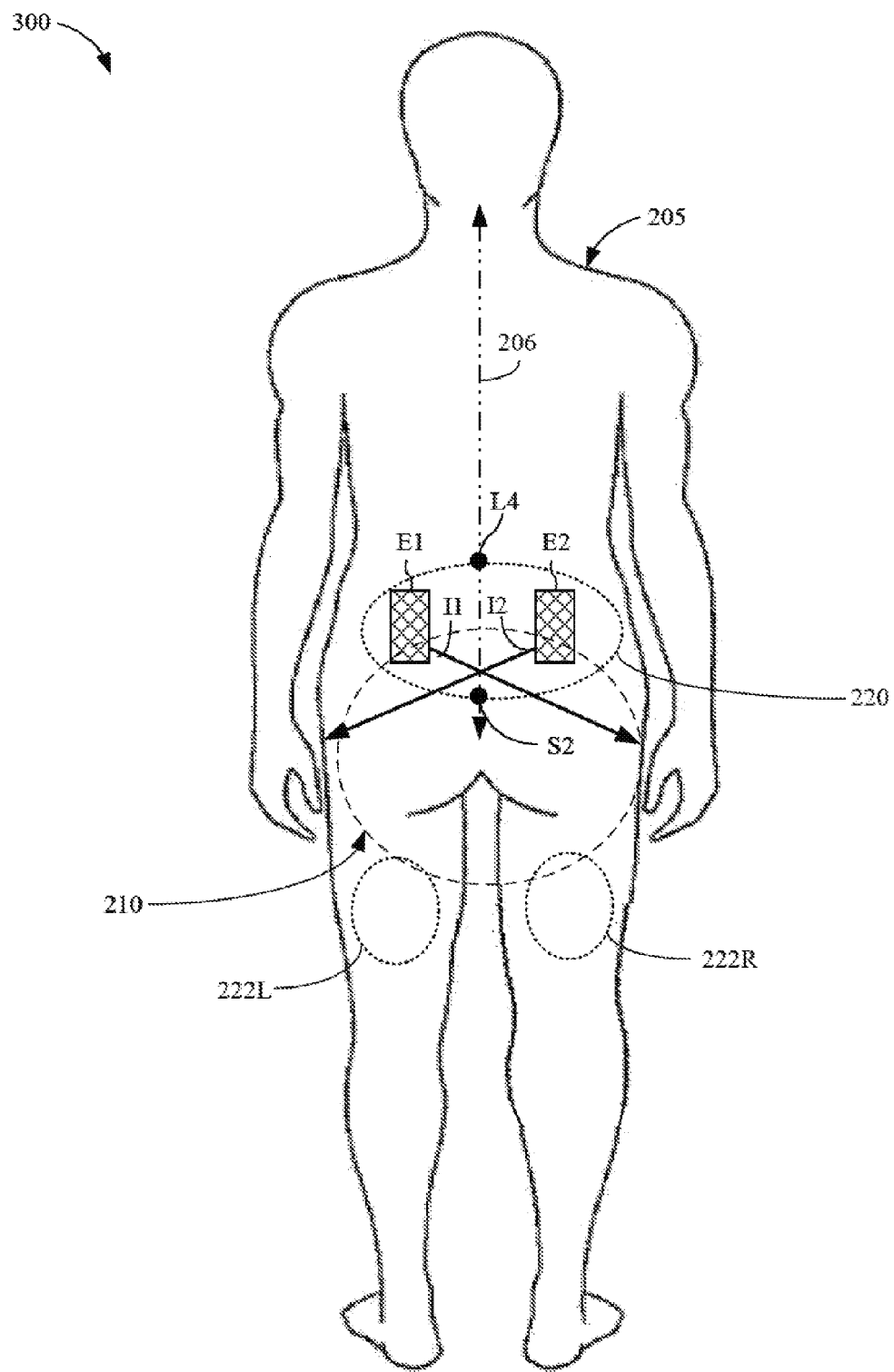
FIGS. 3A-3B depict another example placement of electrodes on a patient in accordance with example embodiments.
Figure 3B:
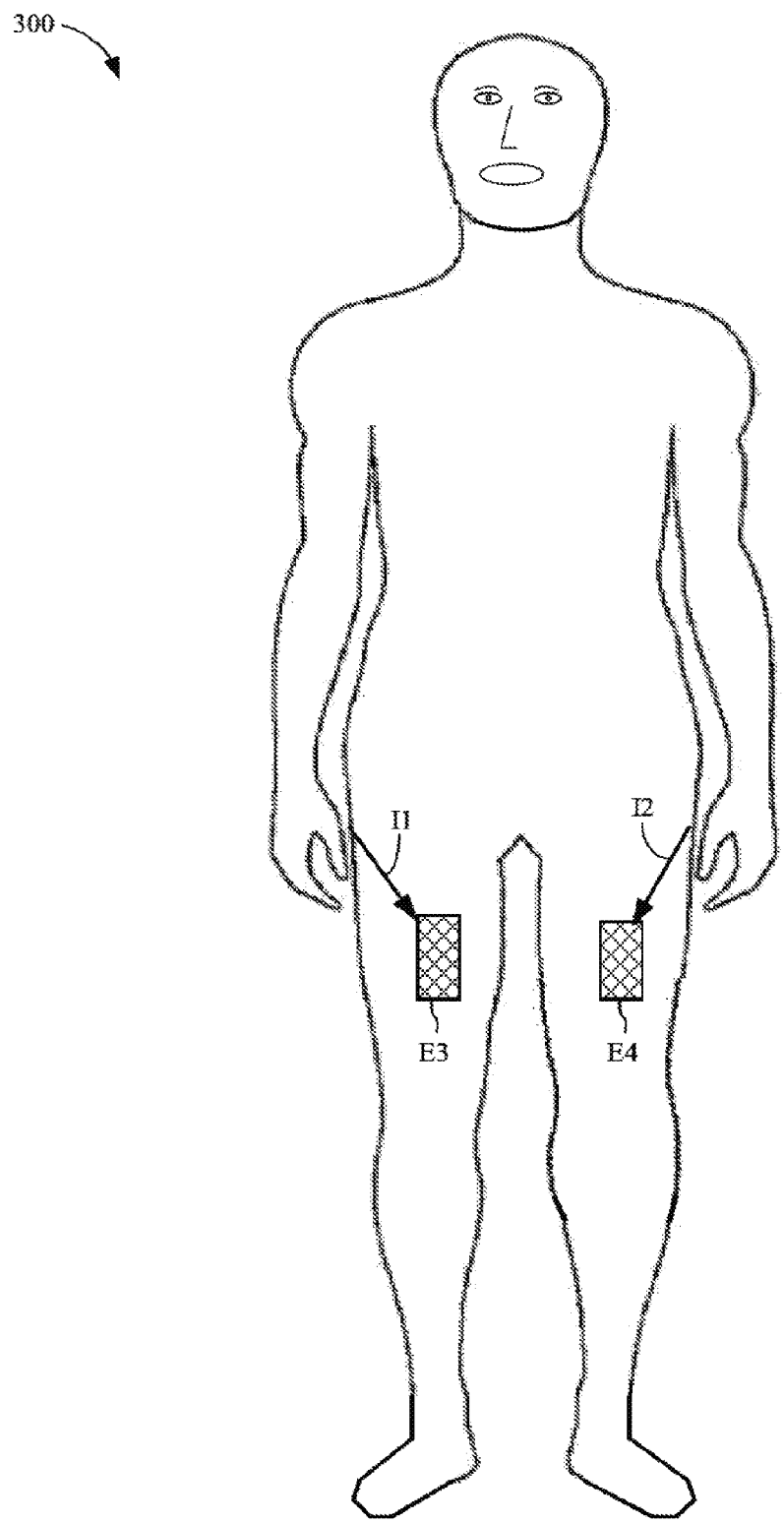

FIGS. 3A-3B show rear and front views of a depiction 300 of another example placement of electrodes E1-E4 on the patient 205. More specifically, the first and second electrodes E1 and E2 are positioned on either side of the patient's spine 206, for example, as described above with respect to FIG. 2A. The third electrode E3 is positioned on a front portion of the right leg between the knee and hip joint, and the fourth electrode E4 is positioned on a front portion of the left leg between the knee and hip joint. For other embodiments, the first and second electrodes E1 and E2 may be positioned in regions of the patient's back higher than L4 or lower than S2, and the third and fourth electrodes E3 and E4 may be positioned either closer to the buttocks or closer to the knees, for example, as may depend upon the electrical, nerve, bone, and/or other characteristics of a given patient.

In operation, the first and third electrodes E1 and E3 are connected to the control unit 120 in a manner that allows a first set of the stimulation waveforms generated by the control unit 120 to transcutaneously apply a first electrical current I1 between the first and third electrodes E1 and E3, and the second and fourth electrodes E2 and E4 are connected to the control unit 120 in a manner that allows a second set of the stimulation waveforms generated by the control unit 120 to transcutaneously apply a second electrical current I2 between the second and fourth electrodes E2 and E4. As depicted in FIGS. 3A-3B, the first electrical current I1 is transcutaneously applied in a first substantially diagonal direction between the first and third electrodes E1 and E3 and travels across the patient's sacral region 210 and around the patient's right hip to reach the third electrode E3 on the patient's right thigh; the second electrical current I2 is transcutaneously applied in a second substantially diagonal direction between the second and fourth electrodes E2 and E4 and travels across the patient's sacral region 210 and around the patient's left hip to reach the fourth electrode E4 on the patient's left thigh.

At least one unexpected result of the transcutaneous application of the electrical currents I1 and I2 depicted in FIGS. 3A-3B is the significant reduction in severity and frequency of involuntary leg twitching and/or leg jerking associated with RLS. More specifically, Applicant believes that the transcutaneous application of electrical currents in the pattern depicted in FIGS. 3A-3B may target and electrically stimulate the femoral nerve, which exits the spinal column between L2-L4 and controls the movement of various muscles within each leg. Thus, by electrically stimulating the femoral nerve, undesirable electrical signals (e.g., errantly transmitted by the brain during the brain's transition from an awake state to a sleep state) that would otherwise cause involuntary leg movements (e.g., twitching and jerking) may be dampened or completely overridden. The dampening of such undesirable electrical signals in the femoral nerves may reduce the onset, severity, frequency, duration, and/or cessation of involuntary leg twitching, leg jerking, and/or other periodic limb movements associated with RLS; overriding such undesirable electrical signals in the femoral nerves may eliminate the onset of such involuntary leg twitching, leg jerking, and/or other periodic limb movements associated with RLS.

Figure 4A:
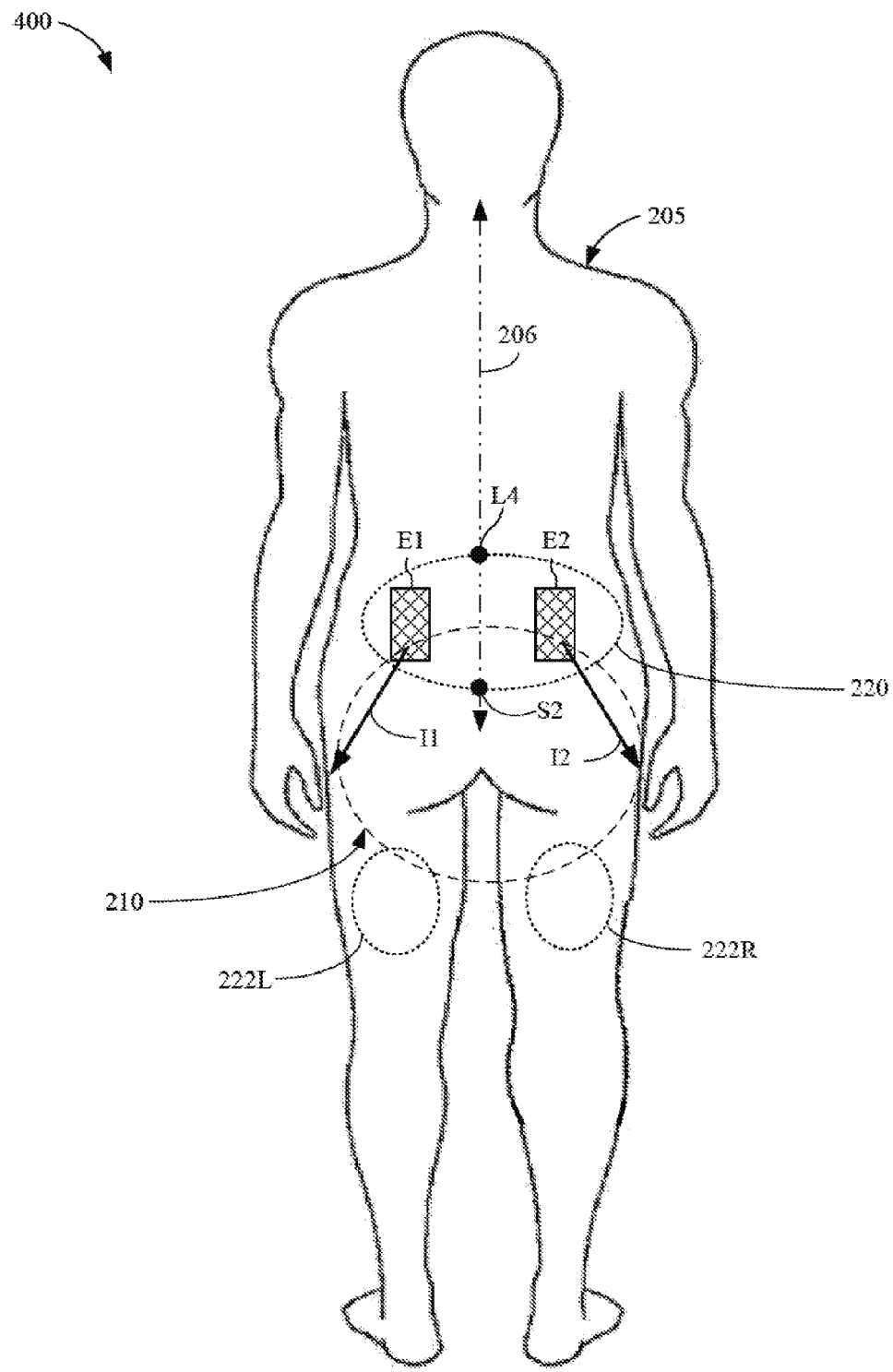
FIGS. 4A-4B depict another example placement of electrodes on a patient in accordance with example embodiments.
Figure 4B:
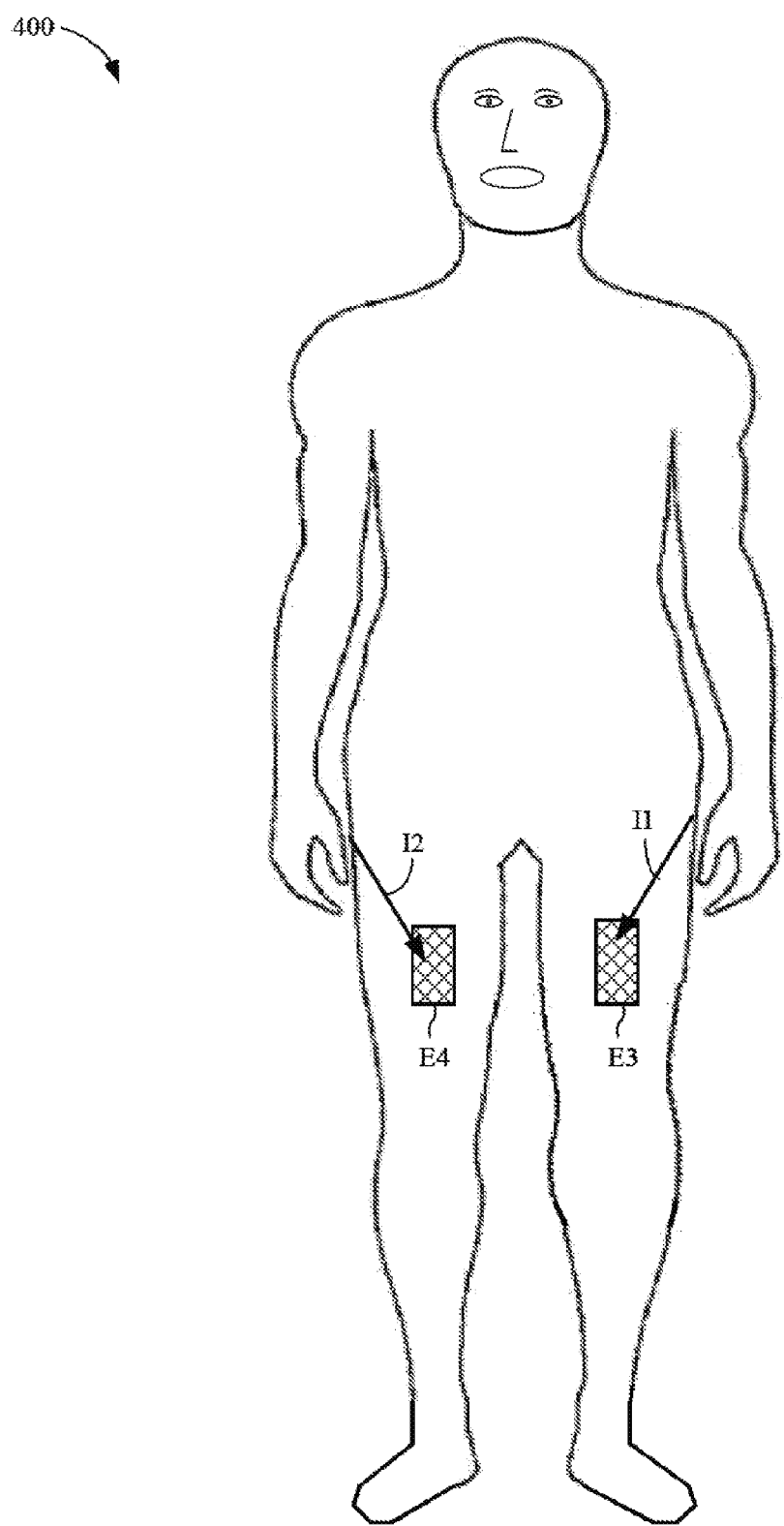

FIGS. 4A-4B show rear and front views of a depiction 400 of yet another example placement of electrodes E1-E4 on the patient 205. More specifically, the first and second electrodes E1 and E2 are positioned on either side of the patient's spine 206, for example, as described above with respect to FIG. 2A. The third electrode E3 is positioned on a front portion of the left leg between the knee and hip joint, and the fourth electrode E4 is positioned on a front portion of the right leg between the knee and hip joint. For other embodiments, the first and second electrodes E1 and E2 may be positioned in regions of the patient's back higher than L4 or lower than S2, and the third and fourth electrodes E3 and E4 may be positioned either closer to the buttocks or closer to the knees, for example, as may depend upon the electrical, nerve, bone, and/or other characteristics of a given patient.

In operation, the first and third electrodes E1 and E3 are connected to the control unit 120 in a manner that allows a first set of the stimulation waveforms generated by the control unit 120 to transcutaneously apply a first electrical current I1 between the first and third electrodes E1 and E3, and the second and fourth electrodes E2 and E4 are connected to the control unit 120 in a manner that allows a second set of the stimulation waveforms generated by the control unit 120 to transcutaneously apply a second electrical current I2 between the second and fourth electrodes E2 and E4. As depicted in FIGS. 4A-4B, the first electrical current I1 is transcutaneously applied in a first substantially diagonal direction between the first and third electrodes E1 and E3 and travels along an edge of the patient's sacral region 210 and around the patient's left hip to reach the third electrode E3 on the patient's left thigh; the second electrical current I2 is transcutaneously applied in a second substantially diagonal direction between the second and fourth electrodes E2 and E4 and travels along an edge of the patient's sacral region 210 and around the patient's right hip to reach the fourth electrode E4 on the patient's right thigh.

Applicant believes that the transcutaneous application of electrical currents in the pattern depicted in FIGS. 4A-4B may also target and electrically stimulate the femoral nerve, which exits the spinal column between L2-L4 and controls the movement of various muscles within each leg. As described above, by electrically stimulating the femoral nerve, undesirable electrical signals (e.g., errantly transmitted by the brain during the brain's transition from an awake state to a sleep state) that would otherwise cause involuntary leg movements (e.g., twitching and jerking) may be dampened or completely overridden, thereby relieve or even eliminating such involuntary leg twitching, leg jerking, and/or other periodic limb movements associated with RLS.

Figure 5A:
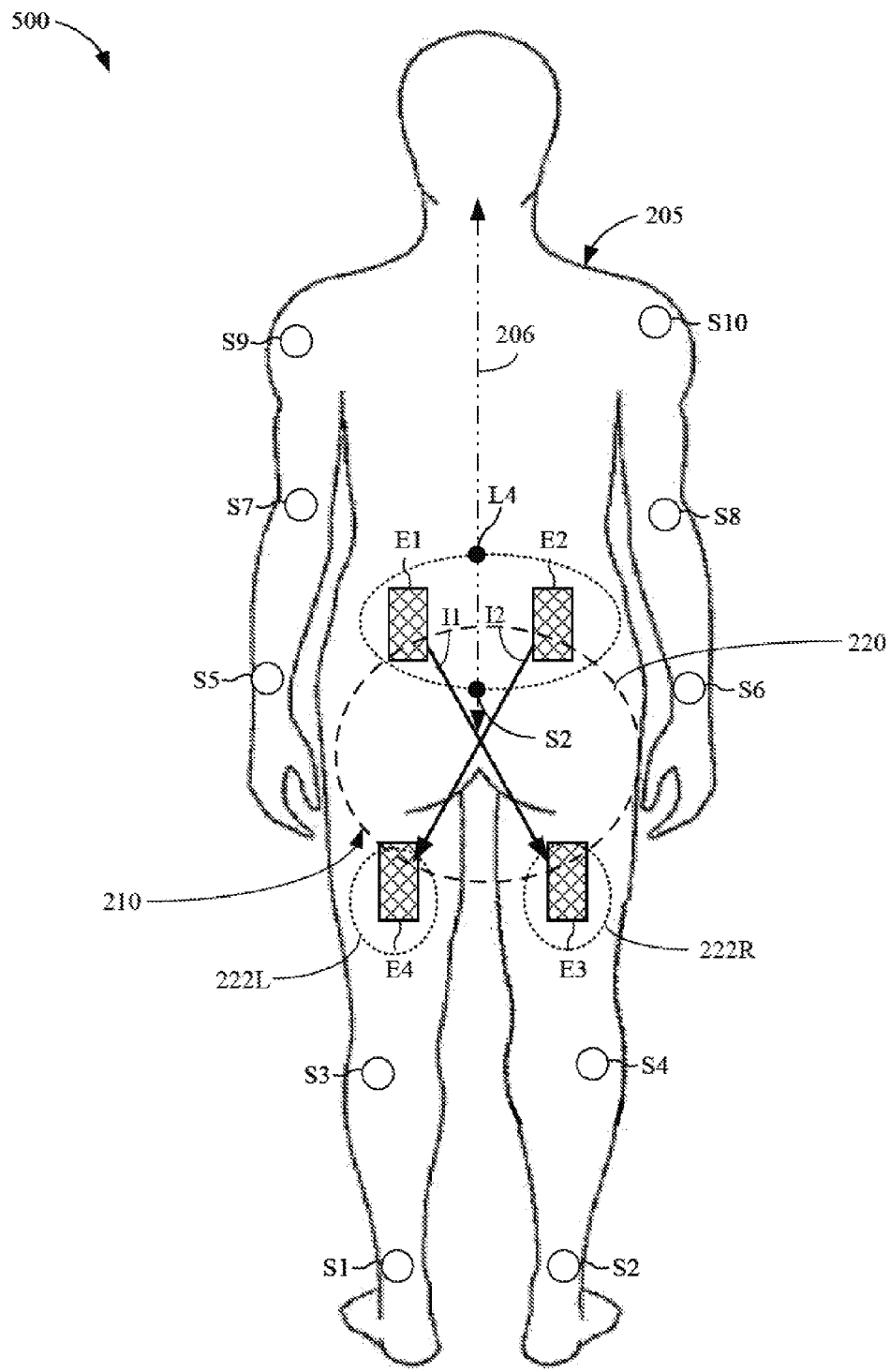
FIGS. 5A-5B depict an example placement of sensors on a patient in accordance with example embodiments.
Figure 5B:
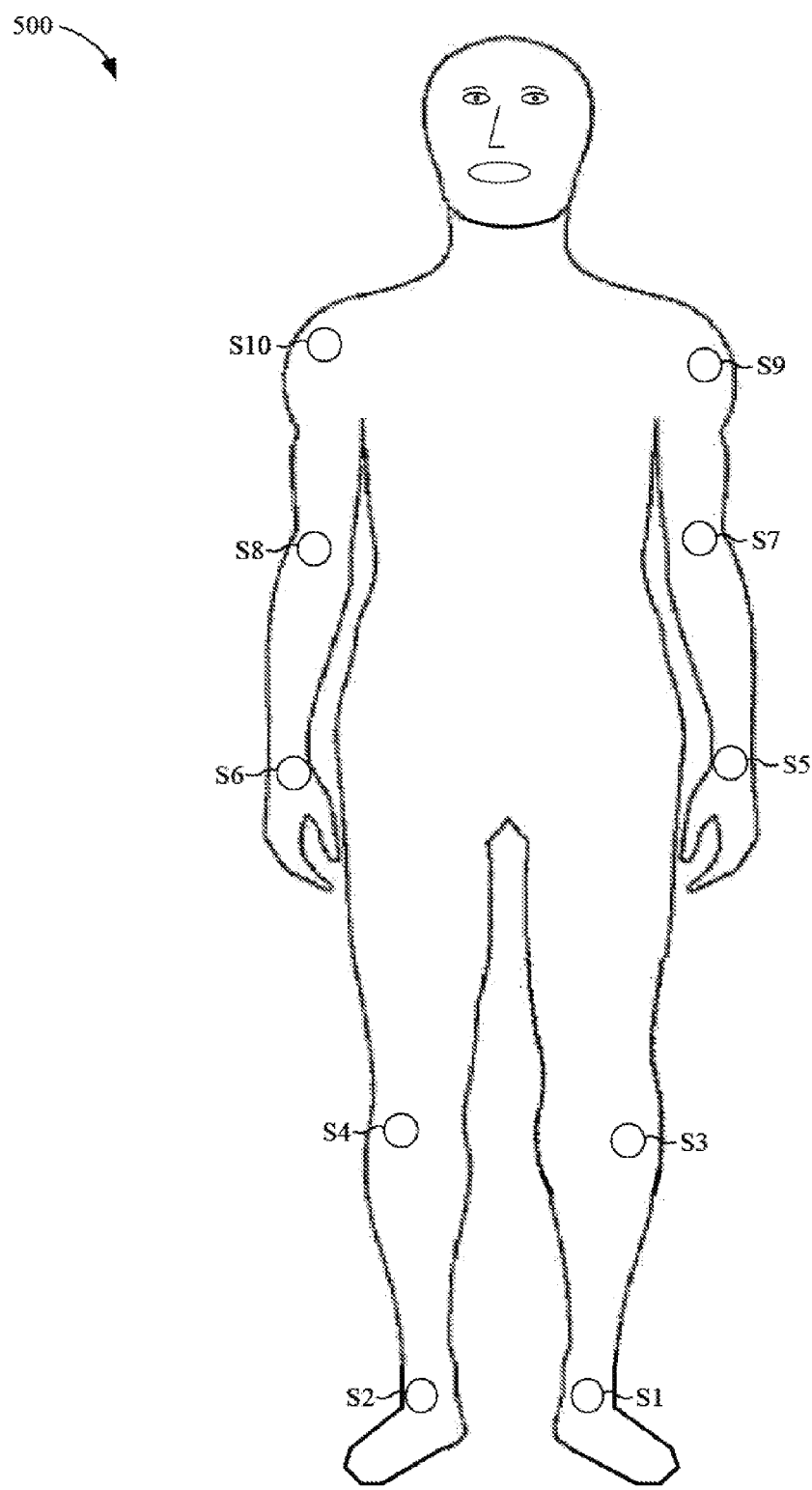

FIGS. 5A-5B show rear and front views of a depiction 500 of an example placement of a number of sensors S1-S10 (as well as the four electrodes E1-E4 depicted in FIG. 2A) on the patient 205. The sensors S1-S10, which are one embodiment of the sensors 130 of FIGS. 1B-1C, are at various locations on the patient's limbs. The sensors S1-S10 may determine positional and movement information of the patient's limbs, and provide the determined positional and movement information as feedback to the control unit 120B or 120C (see also FIGS. 1B and 1C). The control unit 120B or 120C may use the feedback to control and/or adjust the stimulation waveforms provided to the electrodes E1-E4, and may use the feedback to determine efficacy and optimal stimulation waveforms settings and/or optimal positioning of the electrodes E1-E4. The positions of the sensors S1-S10 depicted in FIGS. 5A-5B is merely one example of many possible sensor positional configurations. Further, for actual embodiments, the RLS treatment systems of the example embodiments may include any suitable number of sensors.

Figure 6:
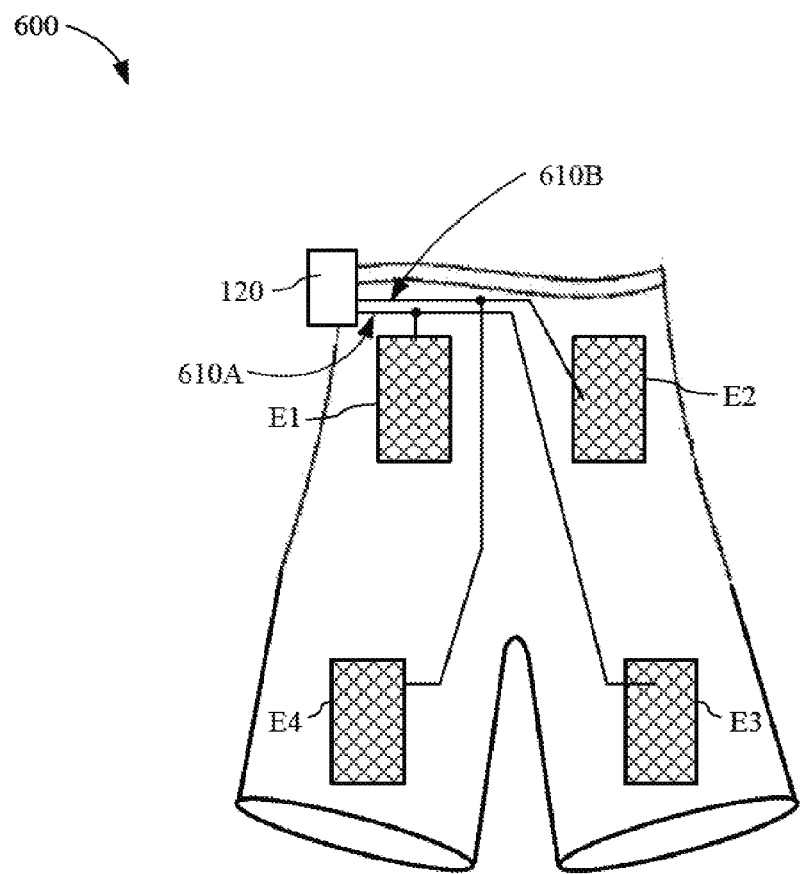
FIG. 6 is a rear plan view of a wearable garment including electrodes positioned in the example pattern depicted in FIG. 2A.

FIG. 6 depicts a wearable garment 600 including electrodes E1-E4 positioned in the example pattern depicted in FIG. 2A. The wearable garment 600, which may resemble underwear, work-out shorts, yoga shorts, yoga pants, and the like, may be manufactured with electrodes E1-E4 embedded therein. The electrodes E1-E4 may be embedded within or removably attached to garment 600 in any suitable manner that ensures contact between electrodes E1-E4 and the RLS patient's skin. For one example, garment 600 may include pockets (not shown for simplicity) into which electrodes E1-E4 may be placed. For another example, garment 600 may include inner adhesive elements (not shown for simplicity) to which electrodes E1-E4 may be attached and adapted to make contact with corresponding portions of the patient's skin, for example, as described above with respect to FIGS. 2A-2B, 3A-3B, 4A-4B, and 5A-5B.

The garment 600 may also include embedded electrical conductors or traces 610A and 610B. In some aspects, electrical trace 610A may provide stimulation waveforms from control unit 120 to electrodes E1 and E3 (e.g., to facilitate the transcutaneous application of first electrical current I1 across the patient's sacral region 210 as described above with respect to FIG. 2A), and electrical trace 610B may provide stimulation waveforms from control unit 120 to electrodes E2 and E4 (e.g., to facilitate the transcutaneous application of second electrical current I2 across the patient's sacral region 210 as described above with respect to FIG. 2A). The control unit 120 may be removably attached to garment 600 in any suitable manner (e.g., on a clip), or may be embedded within, for example, a waist band of garment 600.

Figure 7:
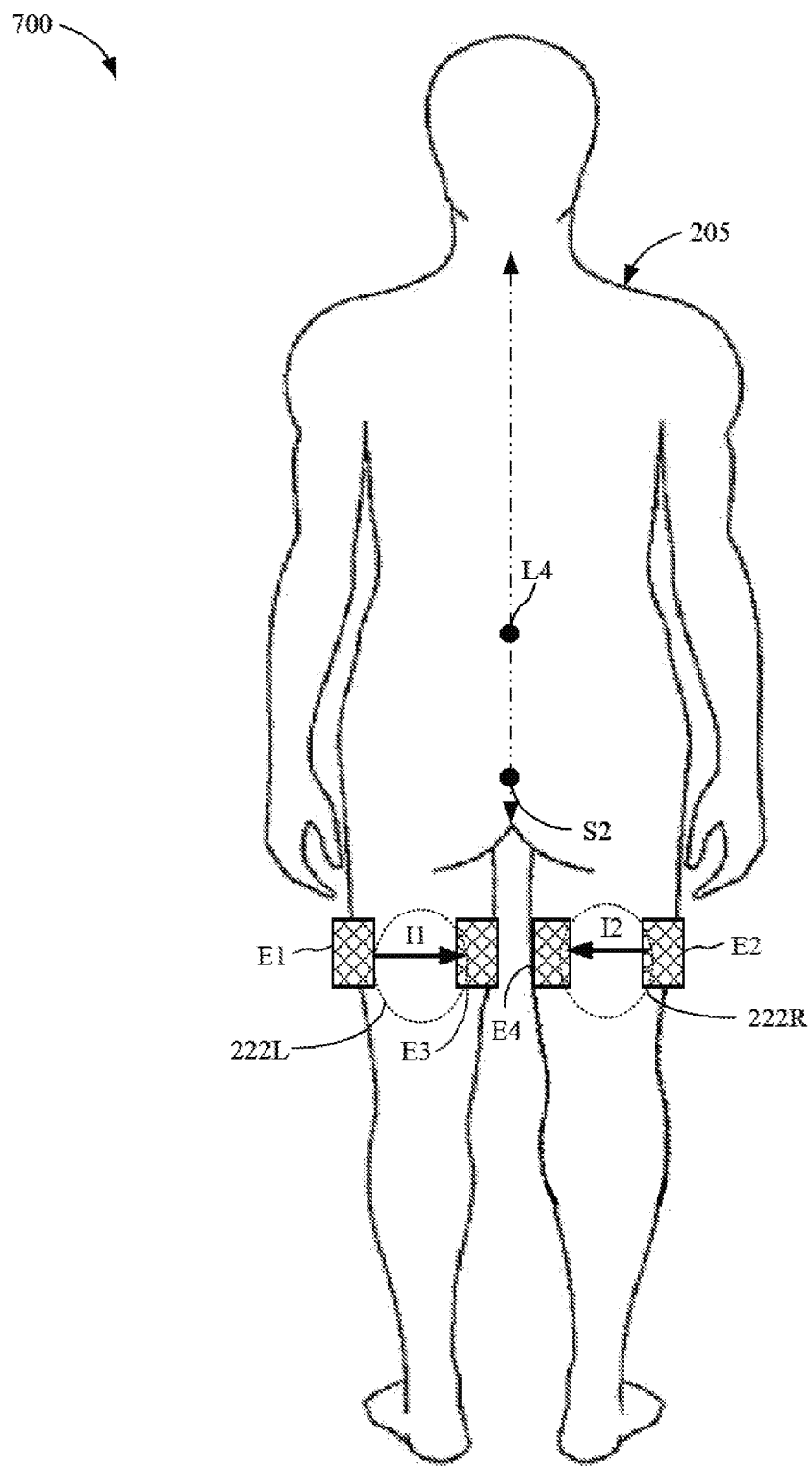
FIG. 7 depicts another example placement of electrodes on a patient in accordance with example embodiments.

FIG. 7 is a depiction 700 of another example placement of electrodes on a patient in accordance with example embodiments. The first and third electrodes E1 and E3 are positioned on lateral portions of the left leg near the sacrum, and the second and fourth electrodes E2 and E4 are positioned on lateral portions of the right leg near the sacrum (although the exact placement of electrodes E1-E4, for the example embodiment of FIG. 7, may vary depending on the particular RLS patient). In operation, the first and third electrodes E1 and E3 are connected to the control unit 120 in a manner that allows a first set of the stimulation waveforms generated by the control unit 120 to transcutaneously apply a first electrical current I1 between the first and third electrodes E1 and E3, and the second and fourth electrodes E2 and E4 are connected to the control unit 120 in a manner that allows a second set of the stimulation waveforms generated by the control unit 120 to transcutaneously apply a second electrical current I2 between the second and fourth electrodes E2 and E4. As depicted in FIG. 7, the first electrical current I1 is transcutaneously applied in a first substantially lateral direction between the first and third electrodes E1 and E3, and the second electrical current I2 is transcutaneously applied in a second substantially lateral direction between the second and fourth electrodes E2 and E4 (for other embodiments, the direction of currents I1 and I2 may be opposite of that shown in FIG. 7).

Applicant has discovered that the positioning of electrodes E1-E4 depicted in FIG. 7 may relieve the sensations that are often precursors to involuntary leg twitching and/or leg jerking associated with RLS. More specifically, by transcutaneously applying electrical currents in lateral directions across the legs, the resulting electrical stimulation may reduce or eliminate sensations such as the "creepy" or "crawly" feelings often associated with RLS.

Figure 8:
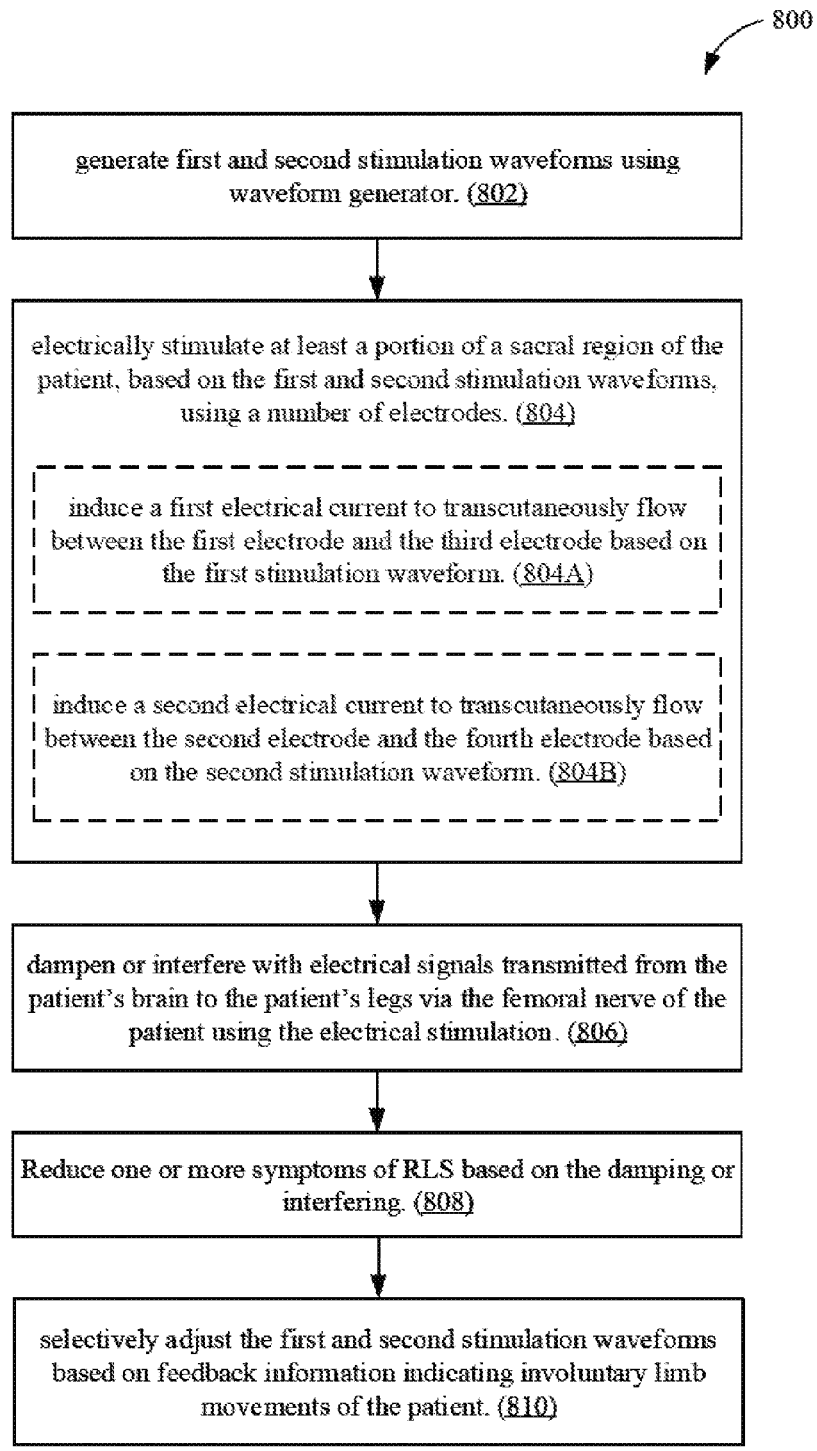
FIG. 8 shows an illustrative flow chart depicting an example operation for treating one or more RLS symptoms of a patient.

FIG. 8 shows an illustrative flow chart depicting an example operation 800 for treating one or more restless leg syndrome (RLS) symptoms of a patient. The example operation 800 may be performed by the system 100 of FIG. 1A, by the system 101 of FIG. 1B, by the system 102 of FIG. 1C, and/or by the garment 600 of FIG. 6. For purposes of discussion herein, the example operation 800 is described below with respect to the system 101 of FIG. 1B and the example placement of electrodes depicted in FIG. 2A.

First, the system 101 may generate first and second stimulation waveforms using waveform generator 128 (802). For some implementations, the first and second stimulation waveforms may each have a frequency of approximately 200 Hz, a pulse width of approximately 250 microseconds, and a current between approximately 8 and 12 milliamps. For other embodiments, other frequencies, pulse widths, and currents may be used.

The system 101 may then electrically stimulate at least a portion of a sacral region 210 of the patient, based on the first and second stimulation waveforms, using a number of electrodes (804). The electrical stimulation may be configured to target the femoral nerve of the patient. For some implementations, the system may include four electrodes (e.g., a first electrode E1, a second electrode E2, a third electrode E3, and a fourth electrode E4). In some aspects, the electrically stimulating may include inducing a first electrical current to transcutaneously flow between the first electrode and the third electrode based on the first stimulation waveform (804A), and inducing a second electrical current to transcutaneously flow between the second electrode and the fourth electrode based on the second stimulation waveform (804B).

Next, the system 101 may dampen or interfere with electrical signals transmitted from the patient's brain to the patient's legs via the femoral nerve of the patient using the electrical stimulation (806). As described above, transcutaneously applying electrical currents in complementary and substantially diagonal directions (e.g., in a criss-cross pattern) across the sacral region of a patient may dampen undesirable electrical signals transmitted from the patient's brain to the patient's legs.

Finally, the system 101 may reduce one or more symptoms of RLS based on the damping or interfering (808). As described above, dampening or interfering with electrical signals transmitted from the patient's brain via the femoral nerve may reduce the severity and frequency of involuntary leg twitching and/or leg jerking. In some instances, the electrical currents transcutaneously applied by the example embodiments may prevent such undesirable electrical signals originating in the patient's brain from reaching the patient's legs, thereby eliminating such involuntary leg twitching and/or leg jerking altogether.

For at least some embodiments, the system 101 may selectively adjust the first and second stimulation waveforms based on feedback information indicating involuntary limb movements of the patient (810). As described above, the system 101 may commence, adjust, and/or terminate the transcutaneous application of electrical currents by the electrodes, for example, by adjusting the stimulation waveforms provided to the electrodes.

Those of skill in the art will appreciate that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Further, those of skill in the art will appreciate that the various illustrative logical blocks, modules, circuits, and algorithm steps described in connection with the aspects disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the disclosure.

The methods, sequences or algorithms described in connection with the aspects disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor.

Accordingly, one aspect of the disclosure can include a non-transitory computer readable media embodying a method for time and frequency synchronization in non-geosynchronous satellite communication systems. The term "non-transitory" does not exclude any physical storage medium or memory and particularly does not exclude dynamic memory (e.g., conventional random access memory (RAM)) but rather excludes only the interpretation that the medium can be construed as a transitory propagating signal.

While the foregoing disclosure shows illustrative aspects, it should be noted that various changes and modifications could be made herein without departing from the scope of the appended claims. The functions, steps or actions of the method claims in accordance with aspects described herein need not be performed in any particular order unless expressly stated otherwise. Furthermore, although elements may be described or claimed in the singular, the plural is contemplated unless limitation to the singular is explicitly stated. Accordingly, the disclosure is not limited to the illustrated examples and any means for performing the functionality described herein are included in aspects of the disclosure.

What is claimed is:

1. A method for treating one or more restless leg syndrome (RLS) symptoms of a patient, the method comprising:
    generating first and second stimulation waveforms using a waveform generator;
    electrically stimulating at least a portion of a sacral region of the patient, based on the first and second stimulation waveforms, using at least four electrodes; and
    damping or interfering with electrical signals transmitted along the patient's femoral nerve to the patient's legs based on the electrical stimulation, wherein:
        a first electrode is positioned on a left portion of the patient's lumbar region and configured to receive the first stimulation waveform on a first channel;
        a second electrode is positioned on a right portion of the patient's lumbar region and configured to receive the second stimulation waveform on a second channel separate from the first channel;
        a third electrode is positioned over a hamstring of the patient's right leg and configured to receive the first stimulation waveform on the first channel; and
        a fourth electrode is positioned over a hamstring of the patient's left leg and configured to receive the second stimulation waveform on the second channel.

2. The method of claim 1, wherein each of the first and second stimulation waveforms has a frequency of 250 Hz, a pulse width of 250 microseconds, and a current between 8 and 12 milliamps.

3. The method of claim 1, wherein the electrically stimulating comprises:
    inducing a first electrical current to transcutaneously flow between the first electrode and the third electrode based on the first stimulation waveform; and
    inducing a second electrical current to transcutaneously flow between the second electrode and the fourth electrode based on the second stimulation waveform.

4. The method of claim 3, wherein the first electrical current flows in a first diagonal direction across the sacral region of the patient, and the second electrical current flows in a second diagonal direction across the sacral region of the patient.

5. The method of claim 4, wherein the first diagonal direction is orthogonal to the second diagonal direction.

6. The method of claim 4, wherein the first and second electrical currents are configured to electrically stimulate the femoral nerve or one or more nerves exiting from the patient's spinal column.

7. The method of claim 3, wherein the number of electrodes further comprises fifth, sixth, seventh, and eighth electrodes, and the electrically stimulating further comprises:
    inducing a third electrical current to transcutaneously flow between the fifth electrode and the eighth electrode based on the first stimulation waveform; and
    inducing a fourth electrical current to transcutaneously flow between the sixth electrode and the seventh electrode based on the second stimulation waveform.

8. The method of claim 7, wherein:
    the fifth electrode is positioned on the left portion of the patient's lumbar region above the first electrode;
    the sixth electrode is positioned on the right portion of the patient's lumbar region above the second electrode;
    the seventh electrode is positioned over the hamstring of the patient's right leg and below the fourth electrode; and
    the eight electrode is positioned over the hamstring of the patient's left leg and below the third electrode.

9. The method of claim 7, wherein the first and second electrical signals comprise a first set of transcutaneously applied electrical currents, and the third and fourth electrical signals comprise a second set of transcutaneously applied electrical currents that overlap the first set of transcutaneously applied electrical currents.

10. The method of claim 1, wherein:
the first electrode is positioned between the patient's L4 vertebrae and S2 vertebrae; and
the second electrode is positioned between the patient's L4 vertebrae and S2 vertebrae.

11. The method of claim 10, wherein the first electrical current is configured to flow from the first electrode to the third electrode, and the second electrical current is configured to flow from the second electrode to the fourth electrode.

12. The method of claim 10, wherein the first electrical current is configured to flow from the third electrode to the first electrode, and the second electrical current is configured to flow from the fourth electrode to the second electrode.

13. The method of claim 1, wherein the electrical stimulation is configured to target the femoral nerve.

14. The method of claim 1, further comprising:
reducing one or more symptoms of RLS based on damping or interfering with the electrical signals.

15. The method of claim 1, further comprising:
selectively adjusting the first and second stimulation waveforms based on feedback information indicating involuntary limb movements of the patient.

16. The method of claim 1, further comprising:
receiving, from a wireless communication device, one or more control signals configured to selectively start, stop, or adjust electrical stimulation of the portion of the sacral region.

17. The method of claim 16, further comprising:
transmitting feedback information from the number of electrodes to the wireless communication device, wherein the control signals are based at least in part on the feedback information.

18. The method of claim 1, wherein at least some of the electrodes are disposed within a wearable garment.

19. A method for treating one or more restless leg syndrome (RLS) symptoms of a patient, the method comprising:
generating first and second stimulation waveforms using a waveform generator;
electrically stimulating at least a portion of a sacral region of the patient, based on the first and second stimulation waveforms, using at least four electrodes;
damping or interfering with electrical signals transmitted along the patient's femoral nerve to the patient's legs based on the electrical stimulation; and
reducing one or more symptoms of RLS based on the damping or interfering with the electrical signals, wherein:
a first electrode is positioned on a left portion of the patient's lumbar region and configured to receive the first stimulation waveform on a first channel;
a second electrode is positioned on a right portion of the patient's lumbar region and configured to receive the second stimulation waveform on a second channel separate from the first channel;
a third electrode is positioned over a quadricep of the patient's right leg and configured to receive the first stimulation waveform on the first channel; and
a fourth electrode is positioned over a quadricep of the patient's left leg and configured to receive the second stimulation waveform on the second channel.

20. The method of claim 19, wherein the first electrical current is configured to flow from the first electrode to the third electrode, and the second electrical current is configured to flow from the second electrode to the fourth electrode.

21. The method of claim 20, wherein the first electrical current is configured to flow across the patient's sacral region and around the patient's right hip, and the second electrical current is configured to flow across the patient's sacral region and around the patient's left hip.

22. The method of claim 19, wherein:
the first electrode is positioned between the patient's L4 vertebrae and S2 vertebrae; and
the second electrode is positioned between the patient's L4 vertebrae and S2 vertebrae.

23. The method of claim 19, wherein the electrical stimulation is configured to target the femoral nerve.

24. The method of claim 19, further comprising:
selectively adjusting the first and second stimulation waveforms based on feedback information indicating involuntary limb movements of the patient.

25. The method of claim 19, further comprising:
receiving, from a wireless communication device, one or more control signals configured to selectively start, stop, or adjust electrical stimulation of the portion of the sacral region.

26. The method of claim 25, further comprising:
transmitting feedback information from the number of electrodes to the wireless communication device, wherein the control signals are based at least in part on the feedback information.

* * * * *